(12) United States Patent
Friedrich et al.

(10) Patent No.: US 7,550,633 B2
(45) Date of Patent: Jun. 23, 2009

(54) METHOD FOR THE PRODUCTION OF ISOPULEGOL

(75) Inventors: Marko Friedrich, Lorsch (DE); Klaus Ebel, Lampertheim (DE); Norbert Götz, Worms (DE)

(73) Assignee: BASF SE, Ludwigshafen (DE)

( * ) Notice: Subject to any disclaimer, the term of this patent is extended or adjusted under 35 U.S.C. 154(b) by 54 days.

(21) Appl. No.: 11/722,395

(22) PCT Filed: Dec. 17, 2005

(86) PCT No.: PCT/EP2005/013628

§ 371 (c)(1),
(2), (4) Date: Jun. 21, 2007

(87) PCT Pub. No.: WO2006/069659

PCT Pub. Date: Jul. 6, 2006

(65) Prior Publication Data

US 2008/0207957 A1    Aug. 28, 2008

(30) Foreign Application Priority Data

Dec. 22, 2004 (DE) .................. 10 2004 063 003

(51) Int. Cl.
*C07C 35/08* (2006.01)
(52) U.S. Cl. ................ 568/828; 568/830; 568/834
(58) Field of Classification Search ............... 568/828, 568/830, 834
See application file for complete search history.

(56) References Cited

U.S. PATENT DOCUMENTS 6,774,269 B2*   8/2004   Iwata et al. .............. 568/828
2002/0133046 A1*   9/2002   Iwata et al. .............. 568/828

FOREIGN PATENT DOCUMENTS

EP           0926117 A1    6/1999
EP           1053974 A1    11/2000
EP           1225163 A2    7/2002
WO    WO-2004/092099 A1   10/2004
WO    WO-2004/101480 A1   11/2004

* cited by examiner

*Primary Examiner*—Sikarl A Witherspoon
(74) *Attorney, Agent, or Firm*—Connolly Bove Lodge & Hutz LLP

(57) ABSTRACT

The present invention relates to a process for the preparation of isopulegol of formula (I):

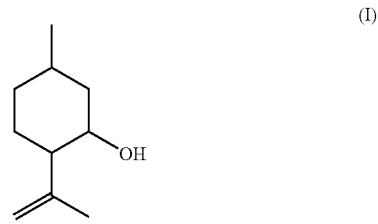

comprising the cyclization of citronellal of formula (II):

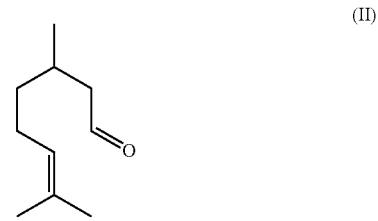

in the presence of a tris(aryloxy)aluminum catalyst, wherein the cyclization is carried out in the presence of
  I. at least one acid and/or
  II. at least one compound selected from the group comprising carboxylic anhydrides, aldehydes, ketones and vinyl ethers.

13 Claims, No Drawings

METHOD FOR THE PRODUCTION OF ISOPULEGOL

RELATED APPLICATIONS

This application is a national stage application (under 35 U.S.C. § 371) of PCT/EP2005/013628 filed Dec. 17, 2005, which claims benefit of German application 10 2004 063 003.8 filed Dec. 22, 2004.

TECHNICAL FIELD OF THE INVENTION

The invention relates to a process for the preparation of isopulegol or mixtures of isopulegol isomers by the cyclization of citronellal in the presence of tris(aryloxy)-aluminum catalysts. The invention relates in particular to a process for the preparation of optically active isopulegol or mixtures of its isomers by the cyclization of optically active citronellal.

Quantitatively, menthol is the most important aroma chemical worldwide. The demand for menthol is still largely met by isolation from natural sources, but there are also synthetic routes to menthol, in some cases in the racemic form and in other cases in the form of the natural enantiomer L-menthol.

An important intermediate for the preparation of optically active menthol is isopulegol, which is conventionally prepared by the cyclizing oxo-ene reaction of citronellal in the presence of Lewis acid catalysts and is conventionally obtained in the form of mixtures of the four diastereoisomers, namely isopulegol, iso-isopulegol, neo-isopulegol and neo-iso-isopulegol.

STATE OF THE ART

EP-A 1,225,163 describes a process for the preparation of isopulegol by the selective cyclization of citronellal in the presence of special tris(2,6-diarylaryloxy)aluminum catalysts, especially the tris(2,6-diphenylphenol)aluminum complex. Of particular note here is the high selectivity of the catalyst in respect of the formation of the desired diastereoisomer (isopulegol).

In carrying out the cyclization reaction in the presence of the catalysts described in EP-A 1,225,163, it has now been observed that it is accompanied by an unwanted and troublesome secondary reaction, namely the formation of citronellyl citronellate of formula (XII):

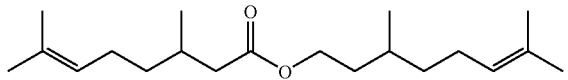
(XII)

or other high-boiling impurities, which is unacceptable given the high yield and selectivity requirements which the aforesaid reaction has to satisfy.

OBJECT OF THE INVENTION

The object of the present invention was to provide a process that made it possible to carry out the cyclization of citronellal to isopulegol in the presence of tris(2,6-diarylaryloxy)aluminum catalysts in such a way as to substantially suppress the formation of higher-boiling reaction products.

DESCRIPTION OF THE INVENTION AND THE PREFERRED EMBODIMENTS

The object was achieved according to the invention by the provision of a process for the preparation of isopulegol of formula (I):

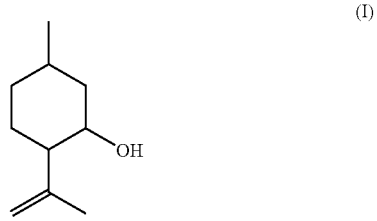
(I)

comprising the cyclization of citronella of formula (II):

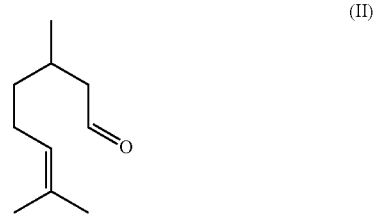
(II)

in the presence of a tris(aryloxy)aluminum catalyst of formula (III):

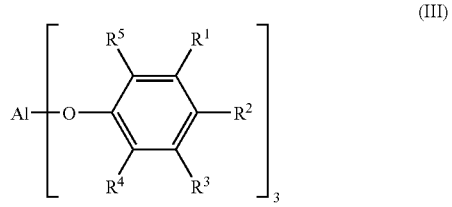
(III)

in which
Al is aluminum,
$R^1, R^2, R^3$ independently of one another can each be hydrogen, a halogen atom, an alkyl radical having 1 to 8 carbon atoms, an alkoxy group having 1 to 8 carbon atoms, a substituted or unsubstituted aryl radical, a dialkylamino group in which each alkyl radical can have 1 to 4 carbon atoms, or a nitro group, and
$R^4, R^5$ independently of one another can each be a halogen atom, an alkyl radical having 1 to 8 carbon atoms, an alkoxy group having 1 to 8 carbon atoms, a dialkylamino group in which each alkyl radical can have 1 to 4 carbon atoms, a nitro group or a substituted or unsubstituted aryl or heteroaryl radical,
wherein the cyclization is carried out in the presence of
  I. at least one acid and/or
  II. at least one compound selected from the group comprising carboxylic anhydrides, aldehydes, ketones and vinyl ethers.

The process according to the invention is distinguished by the fact that the cyclization of citronellal to isopulegol, catalyzed by a tris(aryloxy)aluminum complex of formula (III), is carried out in the presence of at least one acid and/or in the presence of at least one compound selected from the group comprising carboxylic anhydrides, aldehydes, ketones and vinyl ethers. The cyclization is preferably carried out in the presence of at least one compound selected from the group comprising carboxylic anhydrides, aldehydes, ketones and vinyl ethers and preferably selected from the group comprising carboxylic anhydrides, aldehydes and ketones.

The process according to the invention is also suitable for the preparation of isopulegol in optically active form by the cyclization of optically active citronellal. A possible alternative here is to use both the enantiomers of citronellal in a manner according to the invention. It is preferable to use citronellal having an enantiomeric excess of about 90 to about 100% ee, preferably of about 95 to about 99% ee. Particularly preferably, the starting material used to carry out the process according to the invention is D-citronellal of formula (XI):

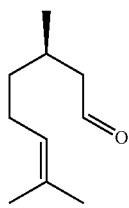

(XI)

to give L-isopulegol of formula (X):

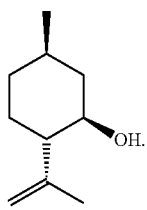

(X)

Independently of the purity or enantiomeric form of the citronellal used, isopulegol is normally obtained in the form of mixtures of the four diastereoisomers, namely isopulegol, iso-isopulegol, neo-isopulegol and neo-iso-isopulegol.

The cyclization process according to the invention for the preparation of isopulegol can be carried out in the presence of one acid or different acids, preferably in the presence of a carboxylic acid having 1 to 20 carbon atoms. Preferred examples of suitable carboxylic acids are formic acid, acetic acid, propionic acid, butyric acid, valeric acid, oxalic acid, malonic acid, succinic acid and citronellic acid, especially acetic acid. Within the framework of the process according to the invention, said carboxylic acids having 1 to 20 carbon atoms can also be used in the form of mixtures with one another.

In another embodiment, the cyclization process according to the invention can advantageously also be carried out in the presence of inorganic acids. Examples of suitable inorganic acids are HCl (hydrochloric acid), which can be used as an aqueous solution, as a solution in organic solvents or in the form of a gas, sulfuric acid, nitric acid, phosphoric acid or mixtures of said acids.

Said acids are conventionally added in amounts of about 0.01 to about 5% by weight, preferably of about 0.1 to about 2.5% by weight, to the citronellal to be converted according to the invention.

In one preferred embodiment according to the invention, the process according to the invention for the preparation of isopulegol by the cyclization of citronellal can also be carried out in the presence of at least one compound selected from the group comprising carboxylic anhydrides, aldehydes, ketones and vinyl ethers.

The compounds belonging to said classes of substances can be used individually or in the form of mixtures with one another. In the latter case, it is preferable to use mixtures consisting of compounds belonging to one class of substances. It is particularly preferable to use individual compounds.

The cyclization according to the invention is preferably carried out in the presence of a carboxylic anhydride of formula (VI):

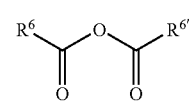

(VI)

in which the radicals $R^6$ and $R^{6'}$ can be identical or different, preferably identical, and are a branched or unbranched $C_1$- to $C_{12}$-alkyl radical or $C_7$- to $C_{12}$-aralkyl radical or a $C_6$- to $C_{10}$-aryl radical, it being possible for said radicals each to have one or more, normally 1 to about 3, identical or different substituents selected from the group comprising $OR^7$, $SR^8$, $NR^9R^{10}$ and halogen, and in which $R^6$ and $R^{6'}$ together can also form a 5- to 8-membered ring which can have one or more, preferably 1 or 2, ethylene double bonds and one or more, preferably 1 or 2, identical or different heteroatoms selected from the group comprising O, S and $NR^{11}$, it being possible for $R^7$, $R^8$, $R^9$, $R^{10}$ and $R^{11}$ independently of one another to be $C_1$- to $C_6$-alkyl, $C_7$- to $C_{12}$-aralkyl and/or substituted or unsubstituted $C_6$- to $C_{10}$-aryl.

By way of example, said radicals $R^7$ to $R^{11}$ may be defined as follows: $C_1$-$C_6$-alkyl, e.g. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethyl-propyl, 1-ethylpropyl, hexyl, 1,1-dimethylropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; $C_7$- to $C_{12}$-aralkyl, e.g. benzyl, 1-phenylethyl and 2-phenylethyl; and $C_6$- to $C_{10}$-aryl such as phenyl or naphthyl.

It is likewise preferable to carry out the process according to the invention in the presence of an aldehyde of formula (VII):

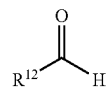

(VII)

in which the radical $R^{12}$ is a branched or unbranched $C_1$ to $C_{12}$-alkyl radical or $C_7$- to $C_{12}$-aralkyl radical or a $C_6$- to $C_{10}$-aryl radical, it being possible for said radicals each to have one or more, preferably 1 to 3, identical or different substituents selected from the group comprising $OR^7$, $SR^8$, $NR^9R^{10}$ and halogen, it being possible for the radicals $R^7$ to $R^{10}$ to be as defined above.

It is likewise preferable to carry out the process according to the invention in the presence of a ketone of formula (VIII):

(VIII)

in which the radicals $R^{13}$ and $R^{14}$ can each be identical or different and are a branched or unbranched $C_1$- to $C_{12}$-alkyl radical or $C_7$- to $C_{12}$-aralkyl radical or a $C_6$- to $C_{10}$-aryl radical, it being possible for said radicals each to have one or more, preferably 1 to 3, identical or different substituents selected from the group comprising $OR^7$, $SR^8$, $NR^9R^{10}$ and halogen, and in which $R^{13}$ and $R^{14}$ together can also form a 5- to 8-membered ring which can have one or more, preferably 1 or 2, ethylenic double bonds and one or more, preferably 1 or 2, identical or different heteroatoms selected from the group comprising O, S and $NR^{11}$, it being possible for the radicals $R^7$ to $R^{11}$ to be as defined above.

Within the framework of the process according to the invention, as an alternative to said carbonyl compounds, it is also possible to use vinyl ethers or vinyl esters of general formula (IX):

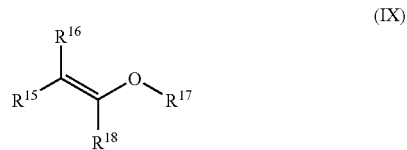

(IX)

in which the radicals $R^{15}$, $R^{16}$, $R^{17}$ and $R^{18}$ independently of one another can each be identical or different and are a branched or unbranched $C_1$- to $C_{12}$-alkyl radical or $C_7$- to $C_{12}$-aralkyl radical or a $C_6$- to $C_{10}$-aryl radical, it being possible for said radicals each to have one or more, preferably 1 to 3, identical or different substituents selected from the group comprising oxo, $OR^7$, $SR^8$, $NR^9R^{10}$ and halogen, and in which $R^{16}$ and $R^{17}$ together can also form a 5- to 8-membered ring which can have one or more, preferably 1 or 2, ethylenic double bonds and one or more, conventionally 1 or 2, identical or different heteroatoms selected from the group comprising O, S and $NR^{11}$, it being possible for the radicals $R^7$ to $R^{11}$ to be as defined above.

$C_1$- to $C_{12}$-alkyl is $C_1$- to $C_6$-alkyl described as above, as well as e.g. heptyl, octyl, nonyl, decyl, undecyl or dodecyl. In cases where two alkyl radicals together form a ring, alkyl radicals are also to be understood as meaning alkylenyl radicals. $C_7$- to $C_{12}$-aralkyl radicals and $C_6$- to $C_{10}$-aryl radicals can be as defined above, for example.

Within the framework of one preferred embodiment, the process according to the invention is carried out in the presence of a carboxylic anhydride of formula (VI) in which the radicals $R^6$ and $R^{6'}$ are identical and are a branched or unbranched $C_1$- to $C_{12}$-alkyl radical or $C_7$- to $C_{12}$-aralkyl radical or a $C_6$ to $C_{10}$-aryl radical, and in which $R^6$ and $R^{6'}$ together can also form a 5- to 8-membered ring which can have one or more, preferably one or 2, ethylenic double bonds and one or more, preferably 1 or 2, identical or different heteroatoms selected from the group comprising O, S and $NR^{11}$, it being possible for the radicals $R^7$ to $R^{11}$ to be as defined above.

It is particularly preferable to use carboxylic anhydrides in which the radicals $R^6$ and $R^{6'}$ are identical and are a branched or unbranched $C_1$- to $C_{12}$-alkyl radical or a $C_6$- to $C_{10}$-aryl radical. The following may be mentioned as examples of particularly preferred carboxylic anhydrides to be used according to the invention: acetic anhydride, propionic anhydride, pivalic anhydride and benzoic anhydride.

Acetaldehyde, propionaldehyde and chloral may be mentioned as examples of aldehydes of formula (VII) which can likewise preferably be used according to the invention.

Within the framework of another preferred embodiment, if the cyclization process according to the invention is carried out in the presence of a ketone of formula (VIII), it is advantageous to use those which have an activated, i.e. electron-deficient, carbonyl group. The following ketones, which are particularly suitable for use within the framework of the process according to the invention, may be mentioned as examples: 1,1,1-trifluoroacetone, 1,1,1-trifluoroacetophenone and hexafluoroacetone.

The following may be mentioned as examples of vinyl ethers of formula (IX) which can likewise preferably be used according to the invention: methyl vinyl ether, ethyl vinyl ether, isobutyl vinyl ether, 3,4-dihydro-2H-pyran and 2-methoxypropene. The corresponding vinyl esters are also suitable for use within the framework of the process according to the invention.

Within the framework of this embodiment of the process according to the invention, said classes of compounds can be used with equally good success. In terms of practicalities, e.g. a higher reaction rate, the use of aldehydes of formula (VII) and/or electron-deficient ketones of formula (VIII) has proved advantageous.

The amount of carboxylic anhydride, aldehyde, ketone and/or vinyl ether to be used according to the invention within the framework of this embodiment can be varied within wide limits and depends on the type of substance used and the degree of purity or the presence of as yet imprecisely identified impurities. Conventionally, said compounds or mixtures thereof are used in an amount of about 0.01 mol % to about 5 mol %, preferably of about 0.1 mol % to about 2 mol %, based on the amount of citronellal used.

The nature of the reaction procedure, e.g. the design of reactors or the order of addition of individual reactants, are not subject to any particular requirements provided oxygen and water are substantially excluded.

To carry out the process according to the invention within the framework of this embodiment, an advantageous procedure is firstly to prepare a solution of the tris(aryloxy)aluminum catalyst of formula (III) or formula (IV), to be used according to the invention, in a suitable solvent as described below. Preferably, according to the invention, a mixture of the racemic or non-racemic citronellal to be cyclized, and the chosen carboxylic anhydride, aldehyde, activated ketone and/or vinyl ether, is then added to said solution. Alternatively, it is also possible, for example, firstly to add the carboxylic anhydride, aldehyde, ketone and/or vinyl ether to the solution of the tris(aryloxy)aluminum catalyst of formula (III) or (IV) to be used according to the invention, and then to add the citronellal to be cyclized.

It has proved advantageous for the citronellal or the mixture of citronellal and the chosen compound to be metered into the catalyst solution or the reaction mixture over a period of about 30 min to about 6 h, preferably over about 2 h to about 3 h. The citronellal can be added as such or in the form of a solution, advantageously in one of the suitable solvents mentioned above. Within the framework of one preferred embodiment of the process according to the invention, a solution of the aryloxy ligand corresponding to the chosen catalyst, in a suitable solvent such as toluene, is prepared first and a toluene solution of a suitable aluminum compound, e.g. trimethylaluminum or triethylaluminum, is then added, expediently with stirring.

The addition of the citronellal to be cyclized, or the mixture of citronellal and the chosen carboxylic anhydride, aldehyde, activated ketone and/or vinyl ether, is advantageously carried out at temperatures ranging from about −40° C. to about 40° C., preferably from about −20° C. to about 20° C. To do this, the prepared solution or suspension of the catalyst to be used according to the invention is advantageously cooled to a temperature within this range, e.g. to a temperature ranging from −10° C. to 10° C., and the other reactants are cooled before being added.

The addition of the mixture of citronellal and the chosen additional compound can be carried out in such a way that the total amount is added to the prepared catalyst solution either all at once, or in portions, or continuously. Suitable solvents are again those mentioned above, especially toluene. Preferably, the citronellal to be cyclized is used in the form of a mixture with the chosen carboxylic anhydride, aldehyde, activated ketone and/or vinyl ether, without the further addition of solvents. If a solvent is used, the total amount of solvent is advantageously chosen so that the volume ratio citronellal to be converted/solvent is about 1:1 to about 1:20, preferably from about 1:1 to about 1:10.

The process according to the invention is carried out in the presence of tris(aryloxy)-aluminum catalysts of formula (III):

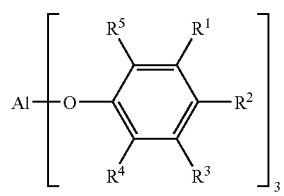

(III)

in which

Al is aluminum, $R^1$, $R^2$, $R^3$ independently of one another can each be hydrogen, a halogen atom, an alkyl radical having 1 to 8 carbon atoms, an alkoxy group having 1 to 8 carbon atoms, a substituted or unsubstituted aryl radical, a dialkylamino group in which each alkyl radical can have 1 to 4 carbon atoms, or a nitro group, and $R^4$, $R^5$ independently of one another can each be a halogen atom, an alkyl radical having 1 to 8 carbon atoms, an alkoxy group having 1 to 8 carbon atoms, a dialkylamino group in which each alkyl radical can have 1 to 4 carbon atoms, a nitro group or a substituted or unsubstituted aryl or heteroaryl radical.

The following meanings of the radicals $R^1$, $R^2$ and $R^3$ may be mentioned by way of example: hydrogen; a halogen atom such as fluorine, chlorine, bromine or iodine; an alkyl group having 1 to 8 carbon atoms, such as methyl, ethyl, propyl, isopropyl, n-butyl, isobutyl, sec-butyl, tert-butyl, pentyl, hexyl, heptyl or octyl; an alkoxy group having 1 to 8 carbon atoms, such as methoxy, ethoxy, propoxy, isopropoxy, butoxy, isobutoxy, sec-butoxy, tert-butoxy, pentoxy, hexyloxy, heptyloxy or octyloxy; a phenyl group which can carry 1 to 5 substituents such as an alkyl group having 1 to 4 carbon atoms (e.g. methyl, ethyl, propyl, isopropyl, n-butyl, isobutyl, sec-butyl, tert-butyl), an alkoxy group having 1 to 4 carbon atoms (e.g. methoxy, ethoxy, propoxy, isopropoxy, butoxy, isobutoxy, sec-butoxy, tert-butoxy), a halogen atom (e.g. fluorine, chlorine, bromine or iodine) or the like; a naphthyl group which can carry 1 to 7 substituents such as an alkyl group having 1 to 4 carbon atoms (e.g. methyl, ethyl, propyl, isopropyl, n-butyl, isobutyl, sec-butyl, tert-butyl), an alkoxy group having 1 to 4 carbon atoms (e.g. methoxy, ethoxy, propoxy, isopropoxy, butoxy, isobutoxy, sec-butoxy, tert-butoxy), a halogen atom (e.g. fluorine, chlorine, bromine or iodine) or the like; a dialkylamino group, it being possible for each alkyl radical to have 1 to 4 carbon atoms, e.g. dimethylamino, diethylamino, dipropylamino, diisopropylamino or dibutylamino; and nitro.

Examples of the radicals $R^4$ and $R^5$ which may be mentioned are the radicals listed above for $R^1$, $R^2$ and $R^3$, except hydrogen, as well as the heteroaryl radicals furyl, thienyl, pyranyl, benzofuryl, isobenzofuryl, benzothienyl, indolyl, isoindolyl, carbazolyl, pyridyl, quinolyl, isoquinolyl or pyrazyl, each of which can carry one or more of the substituents mentioned above.

In one preferred embodiment, the process according to the invention is carried out in the presence of tris(2,6-diarylaryloxy)aluminum catalysts of formula (IV):

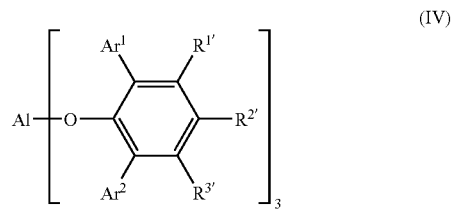

(IV)

in which

Al is aluminum, $Ar^1$ and $Ar^2$ independently of one another are each a substituted or unsubstituted aryl or heteroaryl radical, and $R^{1'}$, $R^{2'}$, $R^{3'}$ independently of one another can each be hydrogen, a halogen atom, an alkyl radical having 1 to 8 carbon atoms, an alkoxy group having 1 to 8 carbon atoms, a substituted or unsubstituted aryl radical, a dialkylamino group in which each alkyl radical can have 1 to 4 carbon atoms, or a nitro group.

Such catalysts and their preparation are described e.g. in EP-A 1 225 163, to which reference is made herein. Conventionally, such catalysts are obtained by reacting the appropriate 2,6-disubstituted phenol ligands with suitable aluminum compounds, e.g. trimethylaluminum, triethylaluminum or triisobutylaluminum hydride.

A preferred catalyst is tris(2,6-diphenylphenol)aluminum (formula (IV) where $R^{1'}$, $R^{2'}$ and $R^{3'}$ are each H and $Ar^1$ and $Ar^2$ are each phenyl), which is obtainable e.g. by reacting 2,6-diphenylphenol with triethylaluminum. Other catalysts are obtainable analogously by processes known to those skilled in the art.

The process according to the invention is conventionally carried out using 0.1 to 5 mol %, preferably 1 to 3 mol %, based on the amount of citronellal to be converted, of one of said catalysts.

Normally, after pretreatment of the citronellal as described above, or after addition of the oxidation products of citronellal, or after addition of the chosen acid or the compound selected from the group comprising carboxylic anhydrides, aldehydes, ketones and vinyl ethers, the catalyst is brought into contact with the educt or a solution of the educt. Suitable solvents which may be mentioned are toluene, ethyl acetate, diethyl ether, methyl tert-butyl ether, dichloromethane, chloroform, carbon tetrachloride, chlorobenzene, isopropyl acetate, hexane, heptane, cyclohexane, THF and acetone. It is also possible to work under solventless conditions.

The cyclization according to the invention is advantageously carried out at temperatures of about −20 to 40° C., preferably at about 0 to about 10° C., and is normally complete after about 1 to about 10 h, often after about 1 to about 5 h. The work-up of the resulting reaction mixture is not critical and can be performed by any of the processes which those skilled in the art deem appropriate.

The cyclization process according to the invention yields isopulegol, conventionally in the form of mixtures of the four diastereoisomers, namely isopulegol, iso-isopulegol, neo-isopulegol and neo-iso-isopulegol, the desired diastereoisomer of isopulegol making up the bulk of the mixture, i.e. normally well above 80% and often well above 90% of the mixture.

The products or product mixtures obtained according to the invention are distinguished by a low content or a substantial to complete absence of unwanted higher-boiling by-products such as the abovementioned citronellyl citronellate of formula (XII):

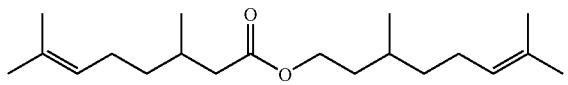
(XII)

Depending on the pretreatment conditions for producing said oxidation products, or depending on the type or amount of oxidation products or carboxylic acids used, the formation of citronellyl citronellate of formula (XII) can be very substantially suppressed, often to a proportion of about 0 to about 5% by weight, based on the total amount of product mixture containing isopulegol.

The described process for the preparation of isopulegol by the cyclization of citronellal in the presence of tris(2,6-diarylaryloxy)aluminum catalysts and oxidation products of citronellal, or organic acids, or the other compounds mentioned, thus provides an economically particularly advantageous route to isopulegol starting from citronellal prepared on the industrial scale. By means that are easy to implement, e.g. without having to distil the starting materials under special conditions, the process makes it possible substantially to suppress the formation of unwanted by-products that are difficult to separate off.

The racemic or non-racemic isopulegol which can be prepared by the process according to the invention constitutes a valuable intermediate for the preparation of racemic or non-racemic menthol, which is one of the most important aroma substances worldwide. Menthol can be obtained from isopulegol by hydrogenation methods known per se to those skilled in the art, especially by catalytic hydrogenation on suitable transition metal catalysts as described e.g. in Pickard et al., J. Chem. Soc. 1920, 1253; Ohloff et al., Chem. Ber. 1962, 95, 1400; Pavia et al., Bull. Soc. Chim. Fr. 1981, 24, Otsuka et al., Synthesis 1991, 665 or EP 1 053 974 A. With the appropriate choice of reaction conditions, the relative or absolute configuration of the isopulegol used is substantially or in many cases completely preserved.

The present invention therefore also relates to a process for the preparation of racemic or non-racemic menthol, comprising the preparation of isopulegol of formula (I) or (X) by the cyclization of racemic or non-racemic isopulegol of formula (II) or (XI) by the process described above, and then hydrogenation, preferably catalytic hydrogenation, of the ethylenic double bond of the isopulegol prepared in this way. In particular, the present invention relates to a process for the preparation of L-(−)-menthol from L-(−)-isopulegol prepared by the cyclization of D-(+)-citronellal according to the invention using the process described above.

EXAMPLES

The Examples which follow serve to illustrate the invention without in any way implying a limitation.

Example 1

General Experimental Instructions:
350 μl (0.66 mmol) of a 0.66 molar solution of triethylaluminum were added at room temperature to 504 mg (2.05 mmol) of 2,6-diphenylphenol and 10 ml of anhydrous toluene. The solution was stirred for 1 h at 25° C. and then cooled to 0° C. and 10.15 g (65.8 mmol) of citronellal precooled to −15° C. were added dropwise. The reaction mixture was stirred for 3 h at 0° C. and 8 ml of 8% sodium hydroxide solution were then added. A sample was taken from the organic phase of the two-phase mixture obtained and was analyzed by gas chromatography as described below. All the experimental values given below are in GC area %.

This procedure yielded a mixture of 4.65% of citronellal, 0.06% of neo-isopulegol, 31.74% of isopulegol, 0.12% of neo-iso-isopulegol, 0.04% of iso-isopulegol and 37.32% of citronellyl citronellate.

GC Analytical Method:
Stationary phase: 30 m DB-WAX, internal diameter: 0.32 mm; flame ionization detector, temperature: 80° C.-230° C.; heating rate: 3° C./min; retention times: Rf (citronellal): 10.5; Rf (neo-isopulegol): 13.24; Rf (isopulegol): 13.58; Rf (neo-iso-isopulegol): 14.64; Rf (iso-isopulegol): 15.28; Rf (citronellyl citronellate): 39.80.

Examples 2 to 4

Citronellal to which citronellic acid had been added in the amount indicated in Table 1, column 2, was converted according to Example 1. The results are collated in Table 1.

TABLE 1

| Example | Addition of citronellic acid | Citronellal | Neo-isopulegol | Isopulegol | Neo-iso-isopulegol | Iso-isopulegol | Ester* |
|---|---|---|---|---|---|---|---|
| 2 | none | 33.41 | 0.09 | 39.39 | 0.36 | 0.05 | 10.19 |
| 3 | 0.1% by weight | 31.81 | 0.10 | 44.02 | 0.33 | 0.06 | 7.89 |
| 4 | 0.5% by weight | 60.79 | 0.08 | 30.22 | 0.29 | 0.04 | 0.74 |

*citronellyl citronellate

Examples 5 to 8

Citronellal to which acetic acid had been added in the amount indicated in Table 2, column 2, was converted according to Example 1. The results are collated in Table 2.

TABLE 2

| Example | Addition of acetic acid | Citronellal | Neo-isopulgol | Isopulegol | Neo-iso-isopulegol | Iso-isopulegol | Ester* |
|---|---|---|---|---|---|---|---|
| 5 | none | 2.67 | — | 6.40 | 0.50 | — | 75.65 |
| 6 | 0.1% by weight | 10.77 | 0.04 | 19.36 | 0.40 | 0.03 | 54.58 |
| 7 | 0.3% by weight | 35.91 | 0.12 | 56.38 | 0.31 | 0.08 | 0.68 |
| 8 | 0.5% by weight | 57.40 | 0.09 | 37.09 | 0.13 | 0.05 | 0.33 |

*citronellyl citronellate

Example 9

Citronellal to which 1.0% by weight of acetic anhydride had been added was converted according to Example 1. The total reaction time was 24 h. The result is collated in Table 3.

TABLE 3

| Time in h | Citronellal | Neo-isopulgol | Isopulegol | Neo-iso-isopulegol | Iso-isopulegol | Citronellol | Ester* |
|---|---|---|---|---|---|---|---|
| 1 | 10.40 | 0.11 | 52.28 | 0.20 | — | — | — |
| 2 | 10.89 | 0.13 | 65.05 | 0.24 | 0.09 | — | — |
| 5 | 13.64 | 0.15 | 74.81 | 0.28 | 0.10 | — | — |
| 6 | 15.71 | 0.15 | 74.13 | 0.27 | 0.10 | — | — |
| 7 | 9.38 | 0.16 | 80.58 | 0.30 | 0.10 | — | — |
| 24 | 1.76 | 0.17 | 88.42 | 0.33 | 0.11 | — | — |

*citronellyl citronellate

We claim:

1. A process for preparing isopulegol having the formula (I)

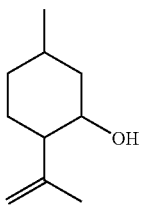

(I)

comprising the step of cyclizing citronellal having the formula (II)

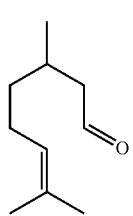

(II)

in the presence of
(a) a tris(aryloxy)aluminum catalyst having the formula (III)

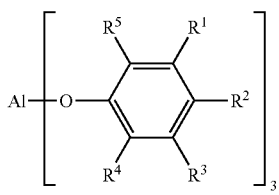

(III)

wherein

Al is aluminum, $R^1$, $R^2$ and $R^3$ identically or differently are hydrogen; halogen; alkyl having up to 8 carbon atoms; alkoxy having up to 8 carbon atoms; substituted or unsubstituted aryl; dialkylamino, wherein each alkyl can have up to 4 carbon atoms; or nitro; and $R^4$ and $R^5$ identically or differently are halogen, alkyl having up to 8 carbon atoms, alkoxy having up to 8 carbon atoms, dialkylamino, wherein each alkyl can have up to 4 carbon atoms; nitro; substituted or unsubstituted aryl; or substituted or unsubstituted heteroaryl;

(b) at least one acid; and/or (c) at least one of carboxylic anhydrides, aldehydes, ketones, and vinyl ethers.

2. The process according to claim 1 wherein said tris(aryloxy)aluminum catalyst is a tris(2,6-diarylaryloxy)aluminum catalyst having the formula (IV)

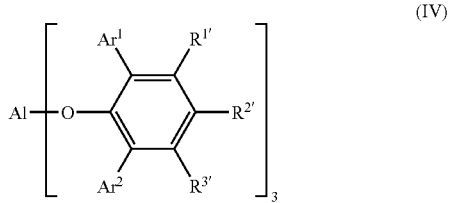
(IV)

wherein
Al is aluminium;
Ar$^1$ and Ar$^2$ identically or differently are substituted or unsubstituted aryl or substituted or unsubstituted heteroaryl; and
R$^{1'}$, R$^{2'}$, and R$^{3'}$
Identically or differently are hydrogen; halogen; alkyl having up to 8 carbon atoms; alkoxy having up to 8 carbon atoms; substituted or unsubstituted aryl; dialkylamino, wherein each alkyl can have up to 4 carbon atoms; or nitro.

3. The process according to claim 1, wherein said at least one acid is an organic acid.

4. The process according to claim 1, wherein said at least one acid is a carboxylic acid having up to 20 carbon atoms.

5. The process according to claim 4, wherein said at least one acid is formic acid, acetic acid, propionic acid, butyric acid, valeric acid, oxalic acid, malonic acid, succinic acid, and/or citronellic acid having the formula (V)

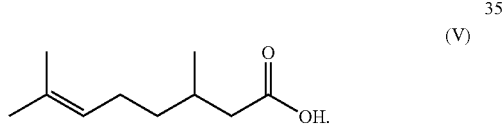
(V)

6. The process according to claim 1, wherein said at least one acid is an inorganic acid.

7. The process according to claim 6, wherein said inorganic acid is hydrochloric acid, sulfuric acid, nitric acid, and/or phosphoric acid.

8. The process according to claim 1, wherein said at least one carboxylic anhydride is a carboxylic anhydride having the formula (VI)

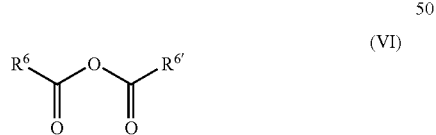
(VI)

wherein
R$^6$ and R$^{6'}$ identically or differently are branched or unbranched C$_1$ to C$_{12}$ alkyl; C$_7$ to C$_{12}$ aralkyl; or C$_6$ to C$_{10}$ aryl; wherein said branched or unbranched C$_1$ to C$_{12}$ alkyl, C$_7$ to C$_{12}$ aralkyl, and C$_6$ to C$_{10}$ aryl are optionally identically or differently substituted with OR$^7$, SR$^8$, NR$^9$R$^{10}$, or halogen, wherein R$^6$ and R$^{6'}$ optionally define a 5 to 8 membered ring optionally having one or more ethylenic double bonds and one or more identical or different heteroatoms selected from the group consisting of O, S, and NR$^{11}$; and wherein R$^7$, R$^8$, R$^9$, R$^{10}$, and R$^{11}$ identically or differently are C$_1$ to C$_6$ alkyl, C$_7$ to C$_{12}$ aralkyl, and/or substituted or unsubstituted C$_6$ to C$_{10}$ aryl;

wherein said at least one aldehyde is an aldehyde having the formula (VII)

(VII)

wherein
R$^{12}$ is a branched or unbranched C$_1$ to C$_{12}$ alkyl; C$_7$ to C$_{12}$ aralkyl; or C$_6$ to C$_{10}$ aryl; wherein said branched or unbranched C$_1$ to C$_{12}$ alkyl, C$_7$ to C$_{12}$ aralkyl, or C$_6$ to C$_{10}$ aryl are optionally identically or differently substituted with one or more OR$^7$, SR$^8$, NR$^9$R$^{10}$, and halogen, wherein R$^7$, R$^8$, R$^9$, and R$^{10}$ identically or differently are C$_1$ to C$_6$ alkyl, C$_7$ to C$_{12}$ aralkyl, and/or substituted or unsubstituted C$_6$ to C$_{10}$ aryl;

wherein said at least one ketone is a ketone having the formula (VIII)

(VIII)

wherein
R$^{13}$ and R$^{14}$ identically or differently are branched or unbranched C$_1$ to C$_{12}$ alkyl; C$_7$ to C$_{12}$ aralkyl; or C$_6$ to C$_{10}$ aryl; wherein said branched or unbranched C$_1$ to C$_{12}$ alkyl, C$_7$ to C$_{12}$ aralkyl, or C$_6$ to C$_{10}$ aryl are optionally identically or differently substituted with OR$^7$, SR$^8$, NR$^9$R$^{10}$, or halogen; wherein R$^{13}$ and R$^{14}$ optionally define a 5 to 8-membered ring having one or more ethylenic double bonds and one or more identical or different heteroatoms selected from the group consisting of O, S, and NR$^1$; and wherein R$^7$, R$^8$, R$^9$, R$^{10}$, and R$^{11}$ identically or differently are C$_1$ to C$_6$ alkyl, C$_7$ to C$_{12}$ aralkyl, and/or substituted or unsubstituted C$_6$ to C$_{10}$ aryl; and wherein said at least one vinyl ether is a vinyl ether having the formula (IX)

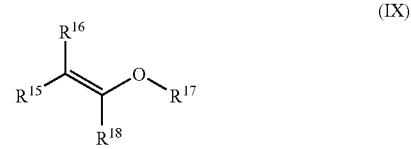
(IX)

wherein
R$^{15}$, R$^{16}$, R$^{17}$, and R$^{18}$
identically or differently are branched or unbranched C$_1$ to C$_{12}$ alkyl; C$_7$ to C$_{12}$ aralkyl; or C$_6$ to C$_{10}$ aryl; wherein said branched or unbranched C$_1$ to C$_{12}$ alkyl, C$_7$ to C$_{12}$ aralkyl, or C$_6$ to C$_{10}$ aryl are optionally identically or differently substituted with oxo, OR$^7$, SR$^8$, NR$^9$R$^{10,}$ or halogen; wherein R$^{16}$ and R$^{17}$ optionally define a 5 to 8 membered ring optionally having one or more ethylenic double bonds and one or more identical or different heteroatoms selected from the group consisting of O, S, and NR$^{11}$; and wherein R$^7$, R$^8$, R$^9$, R$^{10,}$ and R$^{11}$ identically or differently are C$_1$ to C$_6$ alkyl, C$_7$ to C$_{12}$ aralkyl, and/or substituted or unsubstituted C$_6$ to C$_{10}$ aryl.

9. The process according to claim 1, wherein said at least one carboxylic anhydride is acetic anhydride, propionic anhydride, pivalic anhydride, and/or benzoic anhydride.

10. The process according to claim 1, wherein said at least one aldehyde is acetaldehyde, propionaldehyde, or chloral, and said at least one ketone is 1,1,1-trifluoroacetone, 1,1,1-trifluoroacetophenone, or hexafluoroacetone.

11. The process according to claim 1, wherein said isopulegol and said citronellal are optically active.

12. The process according to claim 11, wherein said isopulegol is L-isopulegol having the formula (X)

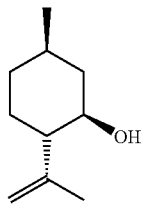

(X)

and said citronellal is D-citronellal having the formula (XI)

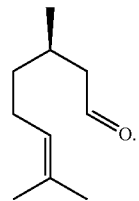

(XI)

13. A process for preparing racemic or optically active menthol, comprising the steps of
 (1) preparing racemic or optically active isopulegol according to the process of claim 1, wherein said citronellal is racemic or optically active; and
 (2) hydrogenating the ethylenic double bond of said racemic or optically active isopulegol.

* * * * *